United States Patent [19]
Schmitt

[11] Patent Number: 5,826,584
[45] Date of Patent: Oct. 27, 1998

[54] DEVICES FOR OCCLUDING CHANNELS IN LIVING MAMMALS

[76] Inventor: Edward E. Schmitt, 2344 Columbia St., Palo Alto, Calif. 94306

[21] Appl. No.: 539,168

[22] Filed: Oct. 4, 1995

Related U.S. Application Data

[62] Division of Ser. No. 939,110, Sep. 2, 1992, Pat. No. 5,469,867.

[51] Int. Cl.$^6$ .................................................. A64B 19/00
[52] U.S. Cl. ............................................................ 128/898
[58] Field of Search ...................... 128/897–99, 830–34, 128/842–43

[56] References Cited

U.S. PATENT DOCUMENTS

| | | |
|---|---|---|
| 3,422,813 | 1/1969 | Braley, Jr. et al. . |
| 3,949,750 | 4/1976 | Freeman . |
| 4,461,295 | 7/1984 | Herrick ................................ 128/303.1 |
| 4,509,504 | 4/1985 | Brundin ..................................... 128/83 |
| 4,660,546 | 4/1987 | Herrick et al. ............................. 128/1 |
| 4,959,048 | 9/1990 | Seder et al. . |
| 5,049,142 | 9/1991 | Herrick et al. ........................... 604/294 |
| 5,053,030 | 10/1991 | Herrick et al. ........................ 604/890.1 |
| 5,065,751 | 11/1991 | Wolf ........................................ 128/831 |
| 5,163,959 | 11/1992 | Herrick ..................................... 623/11 |
| 5,171,270 | 12/1992 | Herrick ....................................... 624/4 |

FOREIGN PATENT DOCUMENTS

| | | |
|---|---|---|
| 2223025 | 9/1988 | United Kingdom . |
| WO81/00701 | 9/1980 | WIPO . |
| WO90/13420 | 4/1990 | WIPO . |

OTHER PUBLICATIONS

J. Poly. Sci. Poly. Physics Ed. 18:2197 (1980) (erroneously typed as 11:2197 in application).
J. Polymer Sci.: Macromolecular Review 8:117–252 (1974).
C. V. Mosby, Body Temperature Regulation, Medical Physiology, 11th ed. Edited by Philip Bard (1961).
Robert W. Lenz, Organic Chemistry of Synthetic High Polymers, John Wiley & Sons, N.Y. (1967) pp. 44–49.
Macromolecules 19:611 (1986).
J. Poly. Sci. 7:3053 (1969).
J. Poly. Sci. 10:3347 (1972).
J. Poly. Sci. 10:1657 (1972).
J. Poly. Sci. 9:3367 (1971).
J. Poly. Sci. 17:991 (1985).
J. Poly. Sci. 60:19 (1962).

(List continued on next page.)

*Primary Examiner*—John P. Lacyk
*Attorney, Agent, or Firm*—Sheldon & Mak

[57] ABSTRACT

A method of blocking channels in a mammal which channels normally carry a material from one point to another is carried out by injecting a heated flowable polymer into the channel and allowing the polymer to cool and solidify, thus creating a plug or channel occluder. The plug can be later removed physically in its solid form or removed gradually by softening and/or fluidizing it by heating and/or chemical means. The channel occluder is preferably comprised of a main chain or side-chain crystallizable polymer but may be comprised of other polymers provided the polymers are formulated to have certain characteristics. The polymers must be solid and/or non-flowable at body temperature or lower and flowable when heated slightly above body temperature, i.e., 10 centigrade degrees or less above body temperature. The polymer is capable of changing quickly from a flowable state to a non-flowable state by moving through only a few centigrade degrees of temperature and is a non-immunogenic, biocompatible material. Typical channels which may be reversibly occluded via the present invention include the vas deferens, the mature sperm excretory channel of the testis; the fallopian tube or oviduct, the viaduct conveying the ovum from the ovary to the uterus; the *canaliculus lacrimalis*, the passageway that allows excess tears to flow from the puncta of the eye to the lacrimal sac; and the cavity of the femoral shaft to fix the stem of replacement hip joint (ball and neck).

19 Claims, 4 Drawing Sheets

OTHER PUBLICATIONS

J. Poly. Sci. 9:3349 (1971).
J. Poly. Sci. 9:1835 (1971).
Macromolecules 12:94 (1979).
J. Am. Chem. Soc. 76:6280 (1954).
Macromolecules 13:12 (1980).
Macromolecules 13:15 (1980).
J. Am. Chem. Soc. 75:3326 (1953).
Macromolecules 18:2141.
PCT Search Report, International Application No. PCT/US93/08245, dated Dec. 29, 1993.

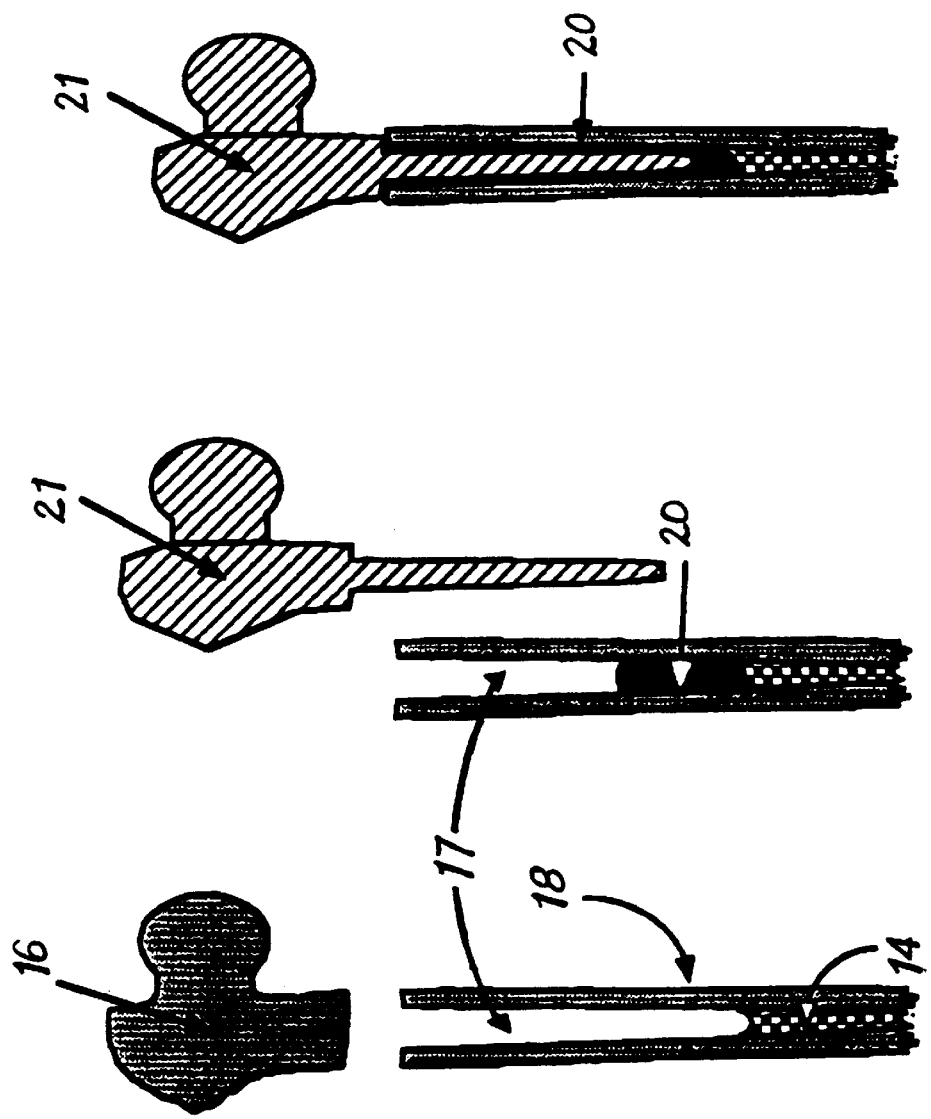

DEVICES FOR OCCLUDING CHANNELS IN LIVING MAMMALS

This is a division of application Ser. No. 07/939,110, filed Sep. 2, 1992 now U.S. Pat. No. 5,469,867.

FIELD OF THE INVENTION

This invention relates generally to the field of medical devices and methods of treatment using such devices, and more particularly relates to thermoplastic polymeric or composite channel occluders and methods of occluding channels in living mammals by forming such channel occluders in situ.

BACKGROUND OF THE INVENTION

All mammals include a variety of channels for moving fluids or materials from one location within the body to another. In general these channels are called tubes, ducts, foramina, cavities, canals and vessels some of which have internal flow controls i.e., sphincters, capillary bed, etc. Specifically these channels include fallopian tubes, nasolacrimal ducts, blood vessels, vas deferens, cavities within the bone and the like. Unless these channels are diseased, surgically altered or damaged in some manner, they continue to provide a means for conducting fluid or material through them for at least part of the time. If they are surgically altered, it may become important to secure a prosthetic element in place. Such channels may be voluntarily closed by the mammal such as by muscular movements or contractions. However, they all remain open part of the time. There are certain advantages to overriding the natural physiology for a sustained period of time and completely closing off particular channels in order to obtain particular desirable results. Depending on the particular channel to be closed, a number of different procedures have been developed in order to temporarily or permanently close such channels, with or without securing prosthesis in place. Some of these procedures are described below.

Blocking the Canaliculus

Mammalian eyes include a complex composition in the form of a tear film. Tears include three basic component layers comprising (1)lipids, (2)an aqueous layer, and (3)mucin. The absence of any one of the layer components causes discomfort and can lead to temporary or permanent dry eye syndromes (SICCA). Each of the component layers has a particular function. The lipid layer prevents evaporation of the tears from the surface of the eye. The aqueous layer is the major component of the tears, and is responsible for providing oxygen to the cornea and contains a number of additional chemical components which are important to a healthy eye. The mucin material provides for interaction between the lipid layer and the aqueous layer and keeps the tears from beading up on the cornea, which will occur in the absence of mucin.

The importance of a tear layer on a healthy mammalian eye can be generally understood based on the above explanation. However, from time to time the eye suffers from a lack of tears (dry eye), which can have a variety of causes but is generally attributed to one or two basic malfunctions. First, the tear ducts leading from the lacrimal glands can be clogged or malfunctioning so that insufficient amounts of tears reach the eye. This was generally thought to be the main reason for dry eye for a considerable period of time. In response, artificial tears were developed and administered to eyes. The relief enjoyed by these tears are short-lived and must be readministered several times each hour. More recently, it has been noted that most tear producing glands can deliver sufficient amounts of tears to the eye, but that the tears are drained away from the eye too quickly, thereby creating a dry eye situation. Accordingly, recent therapies have proceeded on the basis that tear production is adequate in most individuals, and that a significant percentage of dry eye syndrome is caused by excessive tear removal.

Tears are removed from the eye by draining first through upper and lower punctal openings which lead into the canalicular canals. Initial attempts at sealing the puncta and/or the canalicular canals involved stitching the puncta shut or using electrical or laser cauterization to seal the puncta and or canalicular canals. Although such methodology can provide desirable results, the procedure is not reversible without reconstructive surgery. Since it is sometimes difficult to determine whether the drainage is too great or the tear production is too small, irreversible blockage is a condition which is not without risk. If tear production is completely eliminated, it will not solve the problem and the patient would have been exposed to unnecessary expense and trauma. Alternatively, it can result in a situation where normal tear flow is restored and tears continually form on the eye, build up and pour onto the face of the patient. (epiphera)

In order to provide for an autoreversible technique for sealing the puncta or canalicular canals, collagen implants were developed. These implants were designed to be water soluble and were placed in the puncta and/or canalicular canals in order to provide for a test procedure on the patient. Over a period of seven to fourteen days, the implants dissolved. The patient was observed over this time, and it was determined whether it would be desirable to permanently seal the puncta.

Water-insoluble plugs which can be placed in the punctum openings and into vertical sections of the canalicular canals are disclosed within U.S. Pat. No. 3,949,750 to Freeman. Although these plugs are reversible, they tended to become dislodged quite easily. Further, they are somewhat difficult to insert, and occasionally their size and shape can cause tissue damage during insertion or, if they protrude from the puncta, they can cause irritation to the sclera. The tissue of the punctum can also be damaged by being dilated by the plugs over long periods of time.

An improvement on the Freeman plugs is disclosed within U.S. Pat. No. 4,959,048 to Seder et al., issued Sep. 25, 1990. Seder et al. disclose a preformed plug or channel occluder which is somewhat conical in shape, making it possible to insert the occluder into the opening of the punctum more easily than the devices disclosed by Freeman. Further, Seder et al. disclose that variations in the anatomy of individuals make it desirable to provide a series of occluders which are provided in different lengths and/or widths in order to accommodate the anatomical differences. Further, the surface of the plugs may be coated with a lubricant.

Occluding Reproductive Channels

The mature sperm of mammals moves through excretory channels of the testes which are referred to as the vas deferens. A well-known means of male contraception is achieved by carrying out a procedure referred to as a vasectomy, wherein the vas deferens are severed or sealed surgically. Once the channel has been severed, it is difficult to reconnect channels so that they can function properly. In order to attempt to provide some degree of reversibility with respect to this procedure, mechanical valves have been developed and inserted into the vas deferens in a manner which interrupts the flow of sperm through the duct channel. Although this procedure provides a degree of reversibility in that the valves can be opened or closed, the procedure is not without difficulties. First, it is extremely difficult to produce such small valves and to insert them within small channels in a manner which does not damage the channels while making sure that the valves can later be reopened and allow the channels to operate normally. Further, the seal created by such valves is sometimes not complete. Maintaining a healthy, viable seal between living tissue and an inert organic prosthetic device is difficult to accomplish when the device is not designed to conform precisely to the size and shape of the duct channel.

Methods of rendering female mammals infertile include tying ligatures around the fallopian tubes. Thermosetting silicones have been used to fill these tubes to render women infertile. Alternatively, the surfaces of the tubes may be chemically or thermally scarred in such a manner that after healing, the duct channel is closed, preventing the movement of eggs through the channel. In order to reverse such procedures, it is necessary to attempt to remove the damaged portion of the duct channel and surgically connect undamaged ends in a manner so as to provide for a healthy, functionally operating channel. Although a high degree of success is obtained with respect to sealing fallopian tubes, the degree of success with respect to reversing the operation is relatively low.

Closing Off a Blood Supply

In the case where a patient has developed a tumor in an organ, that is inaccessible or the organ is of a nature or in a position that prevents a surgical approach, a method to rid the host of the problem may be to cut off the blood supply and starve the unwanted growth. Rapidly polymerizing monomers such as methyl α-cyanoacrylate can be deposited in the appropriate vessel by means of an appropriately guided cannula or catheter. When the end of the catheter is in the proper position, the monomer is released. Once exposed to the multitudinous supply of nucleophilic natural agents, the monomer polymerizes and effects blockage. However, the monomer itself is toxic and causes acute inflammation and necrosis to the surrounding tissues. The trauma itself enlists a reaction which causes vascularization to the area and soon the tumor is once again well nourished. In the case where a patient has developed an uncontrolled hemorrhage in, perhaps, the brain, there is too much risk to attempt surgical intervention. The safest way to arrive at the site of hemorrhage is again by a fine guided catheter. A rapidly polymerizing monomer such as methyl α-cyanoacrylate can be deposited in the appropriate vessel at the site of hemorrhage. While the polymerizing monomer is effective in shutting down the blood flow through the broken vessel, it sometimes causes the tip of the catheter to become cemented in place.

Correction of Vascular Abnormalities

A condition known as arteriovenous anastomosis (the joining of an artery and a vein) is a serious problem because anastomosis bypasses the intended capillary bed thus starving the cells fed by that system. Once recognized, the surgeon will attempt appropriate measures to correct the condition. Closing off that abnormality by surgery is direct if the area can be accessed. Usually guided catheterization is used when the identified anastomosis is remote or in accessible. Gelling agents are used but they are normally difficult to repair because of the high flow rate through the abnormality. A quick set time creating a permanent plug is very attractive. A cyanoacrylate can be deposited in the appropriate vessel at the site but the method suffers from the risks as described above.

Closing up a Temporary Channel Made for a Cranial Tap

Not all channels need to be provided to the mammalian body by nature. Some could be man-made channels for example, a temporary cranial tap to permit the release of pooled blood between the brain and the skull after a concussion. After the pressure is reduced, the hole must be sealed to prevent the passage of other fluids or bacteria getting into the brain. A plastic shield may be placed over the channel before the skin is pulled over it and sown closed.

Fastening a pin in the lumen of a bone

Broken bones are frequently supported by steel pins placed within the natural lumen of a finger or limb bone. Hip joint replacements usually require that a new ball fitting be placed at the end of the femur by means of a pin or spike. This spike enters the lumen of the femur. In either case, if the fit is not tight, cement or mastic is used to fill in the space between the pin and the bone to keep the pin in position and prohibit it from moving within the lumen.

The above is not, and is not intended to be, an extensive discussion of all of the different types of channels present within living mammals. Further, the above is not, and is not intended to be, a discussion of all the different types of techniques and procedures and devices which can be used to seal such channels in order to obtain results which may be permanently or temporarily desirable. The above merely provides some limited background information on six particular types of channels found in living mammals, which channels are occluded or sealed by medical procedures and/or devices. Further, the above indicates that by carrying out these procedures and/or using these devices, results which are seen as desirable can be obtained. The present inventor endeavors to provide new techniques and devices for sealing channels within mammals which provide a number of advantages.

While the subject of body temperature is a complex one, (see *Body Temperature Regulation*, Medical Physiology, eleventh edition Philip Bard Ed., C. V. Mosby 1961.), several features should be called out. First, the average core temperature of humans is not a very consistent number. It varies for individuals over a range of 36° C. to 38° C. However, normal healthy men or women after vigorous exercise can raise their temperature to as high as 42° C. In the morning when the external surroundings are cool, the body temperature can drop to below 33° C. Extremities such as feet can achieve temperatures of 27° C. when the surroundings are cool.

Second, the temperature at which denaturation of cells occurs varies with the section of the body involved and the time over which the cells are exposed to that heat. The brain is perhaps the most sensitive organ. Brain lesions and heat stroke occur in the range of 42° C. to 44° C. Bones can withstand the exotherm created by polymerizing methylmethacrylate which may exceed 60° C. Most cells can withstand 45° C. temperatures for several minutes without any harmful effects as well as they can tolerate 50° C. for several seconds.

With this background the inventor now can reveal the basis of this disclosure.

SUMMARY OF THE INVENTION

A method of occluding channels in a living mammal by forming channel occluders in situ is disclosed. A variety of channels in living mammals such as the canalicular canals, vas deferens, fallopian tubes, femoral cavity and arteries are all capable of moving fluids or materials from one point to another within a living body. In accordance with the invention, a special polymeric material or composite of such, which exhibits the special characteristic of being a flowable viscous liquid between the average temperature of the site and 50° C. and a rheologically stable solid at or below the average temperature of the site is used. These new techniques and devices must operate and function between the temperature of the host channel and the temperature at which cells and structures begin to disintegrate or denature. In practice, the special polymer or composite is heated to a point where the material is flowable (the preplug) and is then loaded into an injecting device. The injecting device can be maintained warm or above the transition temperature so that the polymeric material or composite of such never cools below transition temperature and solidifies. Also the device and its contents can be alternately cooled and heated so that the polymeric material or composite of such solidifies and then remelts. The process can be repeated as often as is willed. While in a flowable state, the material (preplug) is injected into the living channel which is to be occluded. The polymeric material or a composite of the same cools in place within the channel and solidifies, forming a plug which blocks the channel. The plug can be removed, making the blocking procedure reversible, by physically withdrawing the plug from the channel, heating the plug such as by the application of an electrical heating device which melts the polymer, or applying a lipophilic compound such as an oil or a fatty acid ester which dissolves into the polymer and reduces the melting point of the polymer to a point at or below body temperature, thereby transforming the plug into a flowable fluid that is removable by the normal flow movement characteristics of the channel or by irrigation with saline solution and the like. The channel occluder can be inserted within the canalicular canal in order to prevent dry eye, the vas deferens or fallopian tubes to provide a means of contraception, or inserted within arteries in order to block the blood flow to a tumor area or to plug up a hemorrhage in the brain, liver or spleen or to correct an abnormality such as arteriovenous anastomosis or to close over a tap hole in the skull or to fix a stem, pin or spike within the lumen of a bone. The procedures are primarily designed for human application but can be carried out on other mammals such as canines, race horses and felines which a breeder may wish to render infertile only on a temporary basis or to which a veterinarian may attempt to extend the quality of life or life itself.

An important object of the invention is to provide a method of occluding a channel in a living mammal.

Another important object of the present invention is to provide a channel occluder which is formed in situ in order to block or close a channel in a living mammal such as a human.

An important advantage of the present invention is that the channel occluder can be formed in situ in the lumen of the channel with a minimum degree of trauma to the patient.

Another important advantage of the present invention is that because the channel occluder is formed in situ against the channel wall, a perfect fit is achieved between the plug and the wall thus assuring that no passage of any biological fluids or substance will be allowed.

Another important advantage of the present invention is that because the channel occluder is formed in situ against the channel wall, a perfect fit is achieved between the plug and the normally convoluted wall thus assuring that no movement of the plug will occur with time.

Another important advantage of the invention is that no catalyst, monomers, curing agents or other toxic agents need be present to effect the change between the liquid and solid state of the plug, thus preventing any possible chemical injury to the surrounding tissue.

Another important advantage of the invention is that no exotherm is needed to effect the change between the liquid and solid state of the plug, thus preventing any possible thermal injury to the surrounding tissue.

Another important advantage of the invention is that any variation in the size of the channel from one subject to another can be accommodated because the flowing preplug completely fills the lumen of the channel before it solidifies. There is no need to match a specific internal diameter with different sized plugs. There will always be a perfect fit.

Another important advantage of the present invention is that the channel occluder can be removed from the lumen of the channel without subjecting the channel or the patient to significant trauma and/or discomfort.

An important feature of the present invention is that the channel occluder is comprised of a polymeric or composite material which is flowable at only a few degrees centigrade above body temperature and is solid at body temperature and below, thus preventing any possible injury to the surrounding tissue.

Another important feature of the present invention is that the polymeric or composite material can be selected from a variety and range of crystallization rates from several seconds to several minutes.

Another important feature of the present invention is that the polymeric or composite material can be selected from a group that exhibits a variety and range of temperature transitions from about 30° C. to about 50° C.

Another important feature of the present invention is that the polymeric or composite material is non-immunogenic and biocompatible.

Another advantage of the present invention is that the channel occluder takes on a shape which conforms with the size and shape of the channel being blocked, providing a secure, uniform fit within the duct channel without substantial dilation of the duct channel.

Another important advantage of the invention is that the channel can be blocked with a non-immunogenic, biocompatible polymer or composite without damaging delicate tissue on the internal surface of the duct channel or tissue surrounding the duct channel.

These and other objects, advantages and features of the present invention will become apparent to those persons skilled in the art upon reading the details of the methods, devices and processes as more fully set forth below, reference being made to the accompanying figures forming a part hereof.

BRIEF DESCRIPTION OF THE DRAWINGS

FIG. 5 is a schematic cross sectional view of the human femoral bone that had the defective superior joint process removed and an enlarged channel made within the healthy portion of the bone;

FIG. 6 is a schematic cross sectional view of the human femoral bone that has been partially fitted with the channel occluder of the present invention and, proximal to it, a prosthetic device designed to replace the defective joint process; and FIG. 7 is a schematic cross sectional view of the human femoral bone that has been fitted with the prosthetic device showing the space remaining between the device and the bone has been occluded by the material of the present invention.

DETAILED DESCRIPTION OF PREFERRED EMBODIMENTS OF THE INVENTION

Figure 1:
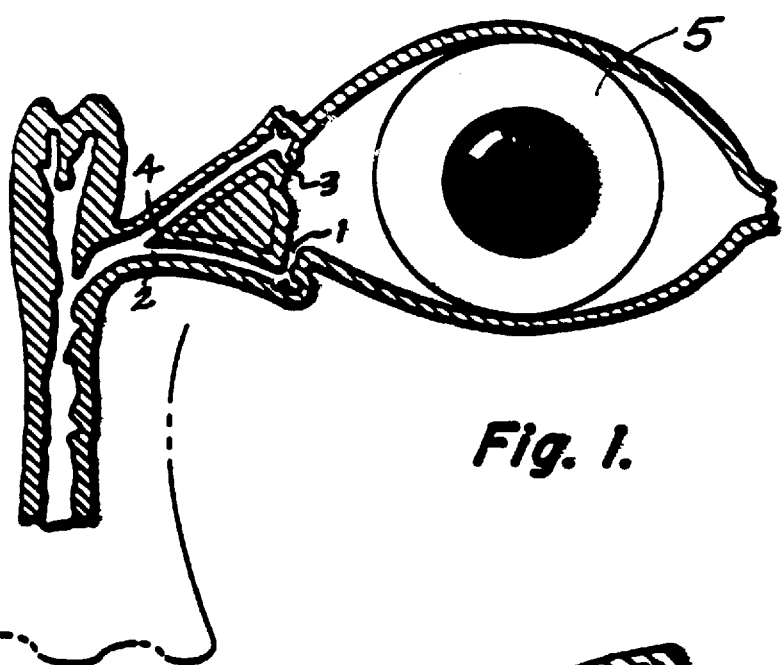
FIG. 1 is a schematic view showing the lacrimal duct channel tear drainage system of a mammalian eye.

Before the present channel occluder and methodologies and processes for making and using same are described, it is to be understood that this invention is not limited to the particular methods, polymers, composites, channels and processes described as such may, of course, vary. It is also to be understood that the terminology used herein is for the purpose of describing particular embodiments only, and is not intended to be limiting since the scope of the present invention will be limited only by the appended claims.

Throughout the disclosure, unless the context clearly dictates otherwise, the terms "a" "an" and "the" include plural referents. Thus, for example, reference to "a polymer" includes mixtures of polymers and statistical mixtures of polymers which include different weight average molecular weight polymers over a range, reference to "an occluder" includes one or more occluders or plugs, and reference to "the channel" includes one or more channels, the same or different types, and so forth.

Unless defined otherwise, all technical terms and scientific terms used herein have the same meaning as commonly understood by one ordinarily skilled in the art to which this invention belongs. Although any methods and materials similar or equivalent to those described herein may be used in the practice or testing of the present invention, preferred methods and materials are described below. All publications mentioned herein are incorporated by reference. Further, specific terminology of particular importance to the description of the invention is defined below.

Definitions

The terms lumen, canal, foramen, tube and duct are used interchangeably herein to describe various channels, passages, openings, cavities or spaces within a living mammalian species through which fluid or material may move from one location to another. The opening is generally cylindrical in dimension with specific non-limiting examples of such channels found within the canalicular canals, vas deferens, fallopian tubes, arteries of the liver, kidney and brain. In most cases, the channels are provided to the mammalian body by nature. However there could be some man-made channels for example, a temporary cranial tap. The material that may pass through the channel does not have to be indigenous to the host either. For example it could be a steel pin within a cavity of a bone. The plug would form between the pin and the bone to keep the pin in position so that it would not pass from the lumen.

The term "occluding a channel" refers to the process of partially and/or completely filling at least a portion or section of a channel, passage, opening, cavity or space with a substance that hinders and/or completely prevents the transport or movement of another substance through the channel. This "other substance" could be biological in origin such as sperm, ova, tears or blood or it could be a prosthetic device such as a metal rod or pin. In preferred embodiments the channel is completely blocked and prevents all flow through.

The term "biologically inert" suggests that no acute physiological activity is observed in response to the presence of the material or substance described as possessing such a property. Examples of unacceptable physiological activity would include surface irritation, cellular edema, etc.

The terms "polymer" and "polymeric material" are used interchangeably herein to refer to materials formed by linking atoms or molecules together in a chain to form a longer molecule, i.e., the polymer. The polymers are preferably biologically inert, biocompatible and non-immunogenic. A range of different polymeric materials can be used in connection with the invention provided they have certain characteristics which include having a melting point which is about or above body temperature but only above body temperature by an amount of 10 centigrade degrees or less. The particularly preferred polymeric materials are biocompatible, non-immunogenic and not subject to substantial degradation under physiological conditions.

The terms "polymer", "polymer composition", and "composite" are interrelated. The "polymer composition" refers to either the polymer of polymeric material itself as defined above or a composite as defined below.

The term "composite" refers to a combination of a polymer with (1) a biologically inert substance that need not qualify as a "polymer" but may have the special characteristics of having a melting point above body temperature and may have the ability to toughen or act as a heat sink for the polymer or be radio-opaque. These biologically inert substances or "fillers" are, for example, spherical particles of gold, silver powder, a radio-opaque pigment or fumed silica. The term "composite" also refers to a combination of a polymer with (2) a biologically active substance that could leach out of the solid occluder once formed in the channel. These biologically active substances could be blood coagulating compounds, spermicides, growth promoting hormones, antibiotics and the like.

The term "melting point" refers to the temperature at which the peak of the endotherm rise is observed when the temperature is raised through this first order transition.

The term "plug" refers to the polymer, polymeric material or composite in its solid form below the crystalline melting point and in the shape and dimensions of the channel which it fills.

The term "preplug" refers to the polymer, polymeric material or composite in its fluid form or state above the crystalline melting point and takes the shape and dimensions of the container or injecting device which holds it.

The term "chamber" refers to central holding portion of the device used to deploy the occluder material.

The term "orifice" refers to the exit port leading from the chamber to the delivery end of the device.

The term "injecting device" includes any device capable of holding or containing the preplug of polymer materials or composites of the present invention in its chamber, while, before or after such a polymer material is heated to a flowable state and is further capable of being used to inject or extrude the polymer materials from that container in which it is held into the duct or channel to be blocked. Specific examples of such devices include all types of hypodermic needles, pointed plastic tip applicators, reservoirs, plungers, release systems and syringes.

Main chain crystallizable polymers (MCC polymers), are useful for this invention are well-known and, some of which, are available commercially. They are reviewed by Robert W. Lenz, "Organic Chemistry of Synthetic High Polymers", John Wiley & Sons, New York, 1967, pp 44–49.

Side chain crystallizable polymers (SCC polymers) are particularly useful for this invention and are sometimes called "comb-like" polymers, are well-known and, some of which, are available commercially. These polymers are reviewed in *J. Polymer Sci.: Macromol. Rev.* 8:117–253 (1974), the disclosure of which is hereby incorporated by reference. In general, these polymers are characterized as having a crystallizable cluster off to the side of the main backbone and can be made in several configurations, i.e. homopolymers, random copolymers, block copolymers and graft copolymers.

Thermoplastic "block" polymers may have enhanced toughness or display good elastic properties below the melting point and are frequently referred to as thermoplastic elastomers or TPE's.

The polymeric hard block used in the synthesis of some of the graft copolymers are referred to as Macromers.

The first order transition is the melting point of the crystalline domains of the polymer. The peak developed in the trace of a differential scanning calorimeter analysis experiment has been used to define this transition.

The flow point of a material is the temperature at which the viscosity is low enough to be observed to flow after the solid is brought through its melting range at a temperature rise of 10° C./minute. For the classes of polymers described in this invention the flow point is generally 2° C. to 6° C. above the first order transition.

General Description of Methodology

In general, the method of the present invention could be used to block any type of channel, i.e., block channels within living and non-living beings of any type and block all types of channels and tubular devices even outside of biological systems. The essence of the invention relates to blocking channels within things, living mammals or human beings in order to prevent movement of a substance into or out of a channel within that host using a material that both flows and solidifies within the very narrow temperature band defined by (1) the normal temperature of the host and (2) the temperature at which thermal damage is done to the walls of the channel thereby obtaining beneficial effects. The invention naturally focuses on and has the greatest need in treating mammalian conditions because of the extreme narrowness of breath between normal body temperature (30°–40° C.) and the temperature range in which thermal denaturation and damage begins. (45° C.–50° C.)

The first step in the method of the invention is to provide a polymer which is preferably a biocompatible, non-immunogenic polymer and to place such polymer within an injecting device of some sort. The polymer should be selected so as to have a melting point (1) sufficiently high that the polymer is a non-flowable solid at the normal temperature of that channel and (2) sufficiently low that melted polymer can be injected into the channel in a flowable form without thermally damaging the cells of the mammal. The polymer can be blended with other materials to produce a composite. The polymer can be formed into a thin rod or cylinder and inserted in a channel as it is undergoing a transition to a fluid form but is preferably injected into the channel. A range of different types of injecting devices can be used such as plastic tubes, catheters, fine cannula, tapered cannula and various types of syringes and hypodermic needles which are generally known to and available to those in the medical profession. The amount of the polymeric material provided in the injecting device will vary somewhat depending on the particular channel to be blocked and the amount and type of blockage desired. Those skilled in the art will be aware of the size of the channel being blocked based on the size of the patient and general knowledge of anatomy and will be able to judge the amount of polymer material to be included within the injecting device. In general, an excess amount of material should be included in the injecting device in order to provide for a certain margin of error.

The polymeric material may be included within the injecting device in a solid form or heated and provided in the injecting device in a flowable form. In one preferred embodiment, the injecting devices can be prepackaged with the polymeric material present therein and thereafter heated in order to make the polymeric material flowable. Heating can be applied (1) from an exterior source such as an air, water or oil bath or an electrical heater. In this case, the injector as well as the occluder material are both heated. Heating can also be applied (2) from an interior source such as a small electrical resistive element at the end of a catheter through which a thin rod of the solid occluder material is being passed or such as a small laser beam directed at the tip of a solid rod of occluder material emerging from the end of a catheter. The injecting device includes an extrusion nozzle which is preferably relatively small in diameter such that it will not seriously damage the channel to be blocked but sufficiently large such that the polymeric material can be freely extruded from the nozzle.

The size of the nozzle is generally related to the inside diameter of the channel into which it is placed. For example, a 24 gauge needle easily fits within the opening of the punctum which leads to the canaliculus. A 2 mm catheter is appropriate for introducing the preplug into the fallopian tubes. A ¼ inch cannula is recommended for introducing the preplug into the inner cavity of an adult humorous. The viscosity limitation of the preplug is dependent upon the size of the orifice that the preplug must pass through. In general, the smaller the orifice the lower the viscosity must be.

Once the polymer has been included within the injecting device and heated to a flowable state, the nozzle of the injecting device such as the tip of a needle or devise is inserted into the channel opening or through the wall of the channel to be blocked and the polymer is injected out of the nozzle into the chamber of the channel. The injection is continued until the desired amount of blockage is obtained. In some instances, it may be desirable to only block part of the channel, i.e., allow partial flow. However, in general, the entire channel is to be blocked. Accordingly, the polymer will generally be injected into the channel so as to completely fill the channel and allow the polymeric material to conform to the internal surface walls of the channel being blocked. Thereafter, the nozzle of the injecting device is withdrawn.

After the polymer has been injected, the remainder of the process will occur without interaction. More specifically, the circulatory system of the mammal will cause a cooling effect on the surrounding tissues which will cool the injected polymer. The polymer is designed such that it cools and solidifies after losing only a small amount of energy, i.e., hardens after decreasing in temperature by only a few centigrade degrees. Usually, the process takes only a few seconds or minutes to occur although there are times when it may be better to take longer, i.e. in the case where the preplug must flow through a long catheter or where a bone must be reset etc. After cooling has taken place, the polymer solidifies within the channel in a manner conforming to the shape of the channel and the channel is blocked. The duct channel occluder formed in the channel can remain in place in the channel over long periods of time. In that the polymer is comprised of a biocompatible, non-immunogenic material, no adverse reaction is obtained. Further, the polymer is designed such that it is not substantially deteriorated under physiological conditions.

One of the important advantages of the method of the present invention is that the duct channel occluder can be readily removed so as to again provide a channel which functions in a normal manner. The duct channel can be removed by a number of different means. Firstly, the duct channel may be removed by simple mechanical extraction. In certain instances, devices such as forceps and/or catheters with various attachment prongs connected thereto can be inserted into the channel and used to attach to the plug and pull the plug out of the channel or force it forward into another chamber where the channel will not be blocked and the plug will not cause any damage. Alternatively, a device such as a wire which acts as a heating coil can be brought into contact with the solidified polymer plug. By heating the material with the heating coil, the temperature of the material is raised above body temperature and above the first order transition point of the polymer so that the polymer again becomes flowable. The heating is continued until the flowable polymer flows from the channel and the channel is reopened to provide normal function. In certain circumstances, the liquid plug can be coaxed out of the channel. It can be made to stick on a fine wire as its cooling, hence the occluder is removed as the wire is withdrawn or it can be suctioned out with a gentle vacuum or it can be forced out using mild pressure created by air or a saline flow.

A particularly preferred method of removing the solidified polymer plug is to inject a lipophilic material such as a naturally occurring oil or a fatty acid ester into the channel in the area surrounding the solidified polymer. The lipophilic material will migrate into and diffuse within the polymeric material. When the lipophilic material and the polymer have interspersed, the lipophilic material will cause the first order transition point of the polymer to be lowered, i.e., causes the plug to have a decreased melting point. Sufficient amounts of the lipophilic material can be added such that the first order transition point of the polymer will drop well below body temperature and the polymer will become flowable. Once the polymer becomes flowable, the natural mechanical movement which occurs within channels of living beings will move the polymer from the channel and the polymer will be removed and the channel will be restored to its normal function.

Treating Dry Eye

As described in the "Background of the Invention" section of this application, the ability to maintain healthy eyes is largely dependent on the ability to maintain a sufficient amount of tears on the surface of the eye. When the amount of tears present is decreased below normal levels, a number of adverse effects can result. Thus, it is desirable to treat the cause of "dry eye". If the "dry eye" is occurring due to the inability of the tear ducts channels to produce any tears, then the present invention cannot be used in order to treat the patient. However, in most cases, the tear ducts channels will produce some tears and in many cases the tear ducts channels will produce sufficient amounts of tears provided the tears are not drained away from the surface of the eye too quickly. When the tear duct channel is producing some tears and/or normal amounts of tears that are being drained away too quickly, the present invention can be used.

By referring to FIG. 1, the lacrimal tear duct channel drainage system of a mammalian eye can be seen. As shown within FIG. 1, the drainage system includes a lower punctum 1 connected to a canalicular channel 2 and an upper punctum 3 connected to a canalicular channel 4. Tears which surround the eye 5 are continually drained from the area surrounding the eye into the punctum 1 and 3 and through the canalicular channels 2 and 4. The tears are eventually drained downward into nasal cavities.

Figure 2:
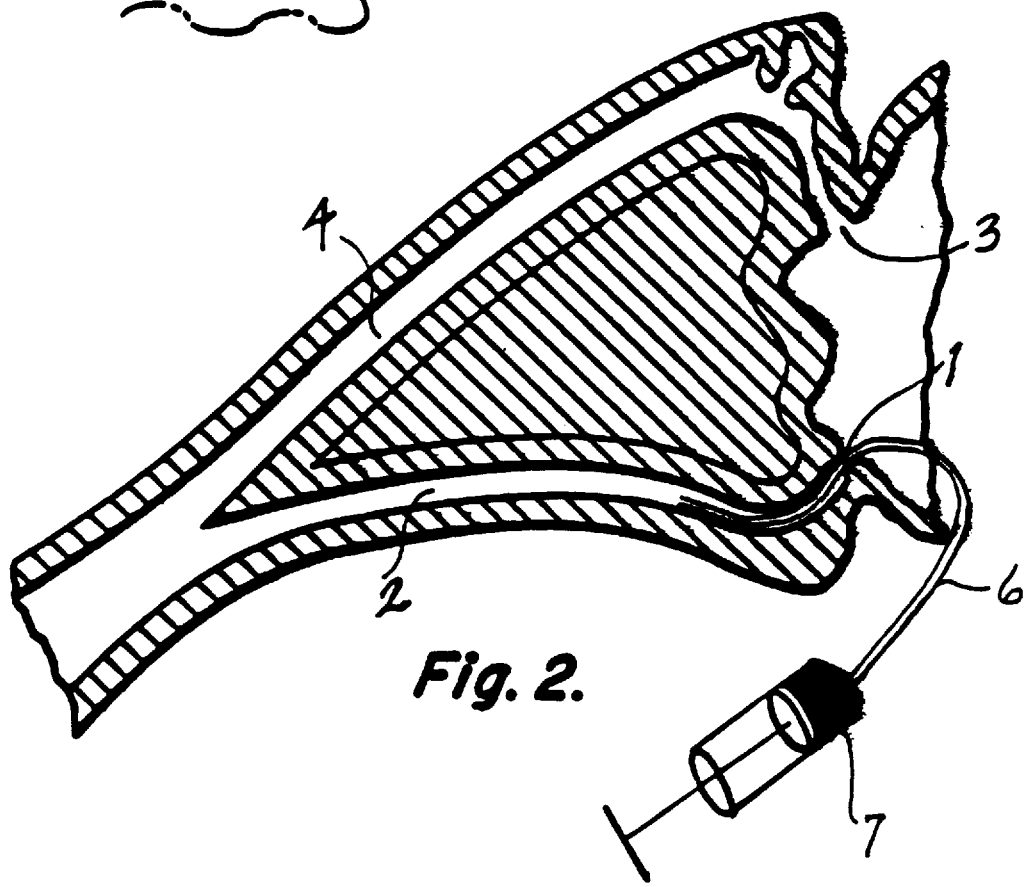
FIG. 2 is a schematic view of an injecting device of the present invention inserting polymeric material into the canalicular canal.
Figure 3:
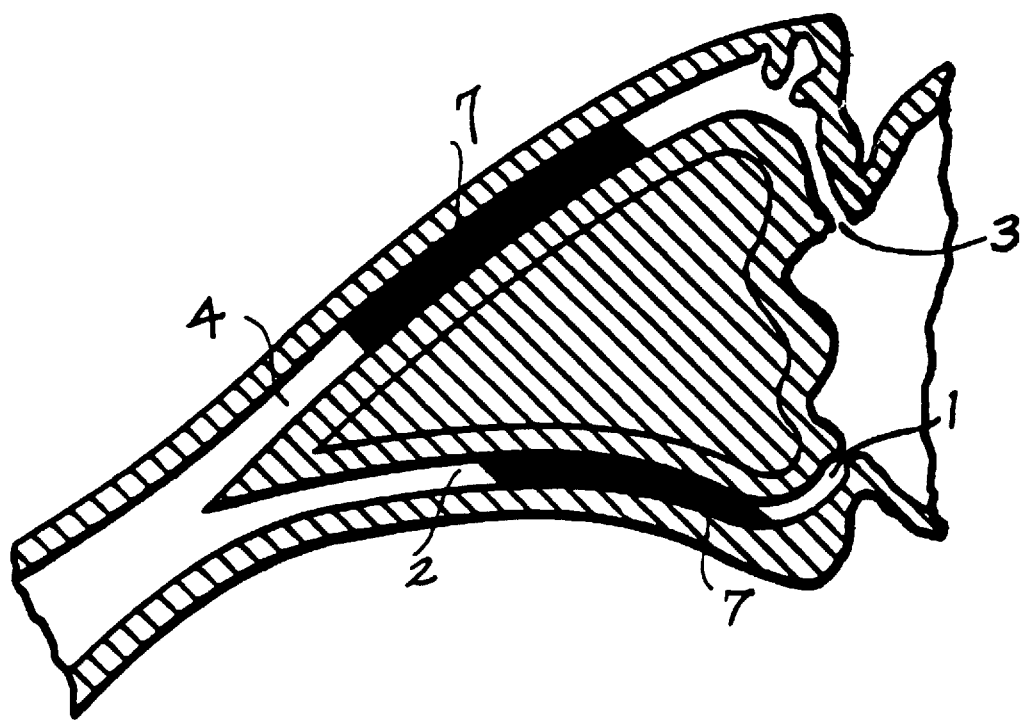
FIG. 3 is a cross sectional schematic view of the canalicular canals blocked with duct channel occluders of the present invention.

When the tear duct channel produces insufficient tears or the punctum or channels become too large and drain the tears too quickly, dry eye results. The present invention can be used in the manner as shown within FIG. 2. As described above, the polymer material is included within an injecting device and heated to a flowable state. The end of the nozzle 6 is shown inserted through the lower punctum 1 and into the canalicular channel 2 where the polymer 7 is injected. Injection of the polymer 7 is continued until the channel 2 is filled. In order to provide for a snug fit, it is possible to inject enough polymer to fill the channel and wait for the polymer to solidify. Thereafter, additional polymer is added in order to overfill the channel while allowing the original polymer deposit to act as a blocking dam. When the channel is overfilled, the polymer forms a plug which conforms to the size of the canalicular channel. As shown within FIG. 3, both canalicular channels 2 and 4 can be filled and completely blocked.

Once the polymer plugs 7 have been placed in the channels 2 and 4, the tears will not drain so quickly form the area around the eye. Thus, the dry eye abnormality should be eliminated. If this treatment is not successful in eliminating the abnormality, it may be desirable to remove the polymeric plugs 7. This can be done in a variety of different means such as those indicated above. One means of eliminating the plugs is to simply use a mechanical means to attempt to extract the plugs outward or to force the plugs downward into the nasal passageways. Alternatively, the plugs can be made flowable by heating or the injection of a material (such as fatty acid esters) which dissolves or decreases the melting point of the plugs below body temperature.

Methods of Contraception

It is well known that male contraception can be carried out by interrupting the flow of sperm through the vas deferens. Further, female contraception can be obtained by interrupting the flow of eggs from the ovarian through the fallopian tubes. Accordingly, the present invention can be utilized in order to temporarily sterilize either male or female mammals by blocking either the vas deferens or fallopian tubes.

The methods of carrying out the contraceptive means of the present invention are substantially the same as the general method described above and the specific method described with respect to blocking the canalicular canals. Those skilled in the art will recognize that there are differences in sizes between the different channels and use appropriate amounts of polymers necessary to block the channels. Further, those skilled in the art will recognize that effective contraception cannot be obtained unless the channels are completely blocked. Accordingly, more diligent efforts should be made in order to completely fill the channels with respect to their circumference but also to fill the channels longitudinally over a great deal or all of their length.

The occlusions of the present invention cause no negative reaction because there are no monomeric or toxic material that could cause irritation nor any exotherm that could thermally denature the surrounding tissue. Thus the closure can be effected with a minimum of trauma to the host.

With respect to male contraception, it should be noted that the vas deferens are maintained at a temperature slightly below body temperature. This should create no problems with respect to the use of the same polymers in that the polymers will solidify at body temperature. Since the vas deferens are maintained at a temperature slightly below 37° C., the polymers should solidify slightly more quickly. However, the polymer will be somewhat more difficult to remove in that it is maintained at a lower temperature, i.e., a temperature slightly below 37° C. Therefore, slightly more heat and/or more fatty acid ester oils may be needed in order to make the polymer flowable and remove the polymer plug from the vas deferens.

Method of Closing off a Supply of Blood

Figure 4:
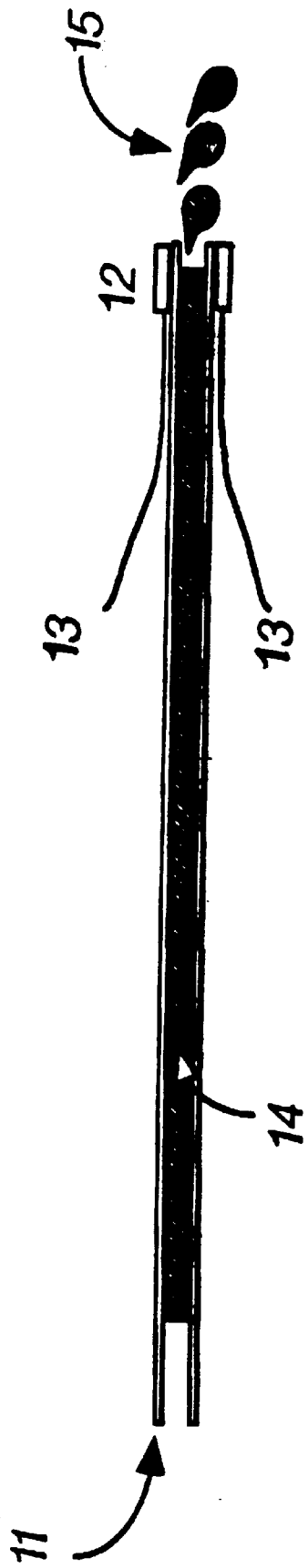
FIG. 4 is a schematic cross sectional view of channel occluder material passing through a fine catheter showing the catheter is fitted with a heater element at the end.

Any of the conditions described earlier, i.e. hemorrhage control, correction of vascular abnormalities, etc. can be treated with the materials disclosed in this invention as described in connection with FIG. 4. The first step is to "snake" a guided catheter 10 into and through the vessels of the circulatory system such that the end of the tip, fitted with a small resistive element 12 and source wires 13, is in near proximity to the defect to be repaired. Next, a solid form of the channel occluder 14 is fed through the catheter until it comes in contact with the heater portion of the catheter. Enough current is passed through the resistive heater to transform the solid channel occluder to its liquid phase 15 as it passes out of the end of the catheter. Thereupon, the liquid flows into the lumen of the vessel or abnormality in need of repair. Heat is transferred from the liquid to the surrounding blood supply and tissue and is transformed back to its solid form that forms a complete seal or occlusion within the vessel wall. The stock solid rod can be fed slowly through the heater until the repair is complete. The catheter can then be removed with assurance that the plug will not attach itself to the catheter end and that the repair has been made. Alternately, a stream of liquid channel occluder can be fed through the catheter.

Method of Affixing a Prosthetic Device within a Bone Channel

A new femoral ball end can be secured in the end of prepared femor using the materials disclosed in this invention. By referring to FIG. 5, and subsequent figures, the procedure can be described. The defective superior joint 16 is removed and a portion of the channel 17 within the longitudinal section of the femor 18 is enlarged at the expense of the bone cells of the femor and the soft tissue 19 normally residing within the femor. Once the channel has been enlarged sufficiently to accept the placement of the prosthetic device, a quantity of polymeric channel occluder 20, shown in FIG. 6, is heated to about 50° C. and injected into the lower end of the enlarged channel. The preheated prosthetic device 21 is plunged into the liquefied occluder mass forcing the mass to flow around the prosthetic device and along the channel walls. In FIG. 7 the prosthetic device is positioned at its proper angle and held in that position for a few minutes. The heat sink capacity of the body continually draws heat from the liquefied channel occluder mass 20 until the temperature of that mass cools below the melting transition temperature. At that time the occluder hardens and the prosthetic device is fixed in place.

Polymeric Materials

A wide range of different polymeric materials can be used in connection with the present invention. However, the materials must be biocompatible and non-immunogenic in order to avoid irritation and adverse reactions when the materials are inserted within the channels to be blocked. In addition to these general characteristics, the polymers must have very specific characteristics with respect to their first order transition point. More specifically, the polymers must be designed such that they are solid and non-flowable at body temperature and below. Preferably, the materials are non-flowable at temperatures 2 to 3 centigrade degrees above body temperature so that they do not become flowable when the individual having the materials therein increases its temperature above normal, i.e., runs a fever or exercises vigorously. The exact temperature at which the polymers should become flowable will vary depending upon the mammal. In humans, the polymers are designed so that they are flowable above 39° C. or at most flowable at a temperature of about 45° C. If the polymer does not become flowable at a temperature of 45° C. and must be heated above that temperature, then the polymer cannot be safely be brought into contact with the mucus membrane surface of the channel to be blocked. Temperatures above 45° C. will frequently damage the tissue and defeat much of the purpose of the invention.

The polymers are also designed such that they can be melted so that they are flowable slightly above body temperature but solidify when cooled to body temperature. Polymeric materials used such as those used in connection with this invention are good diffusers of heat. Accordingly, when brought into contact with the body tissues, they cool quickly and therefore quickly solidify. This is important in order to reduce patient trauma and discomfort.

GENERAL CHARACTERISTICS AND FEATURES OF THE POLYMERS AND THEIR COMPOSITES

Polymers used in this invention preferably have the following attributes:

Sharp melting point behavior. The polymeric materials will be in the liquid state within a 10° C. increase over the initial signs of melting.

The position of the melting phenomenon will fall between 30° C. and 50° C., preferably between 34° C. and 45° C. and even more preferably between 38° C. and 42° C.

Viscosities @ 50° C. (without filler) will be no greater than 1,000,000 centipoise.

The sharpness of the melting point will vary. In general, it will be slightly broader as the molecular weight increases. This is more readily noticed with main chain crystalline polymers than with side chain crystalline polymers.

The most common and most optimum position of the melting point has been found to be at 40°±2° C. This value can be best identified by using the Differential Scanning Calorimeter. The position of the peak endotherm, when raised at 10° C. per minute, is correlated with the melting point.

Viscosity is a subjective feature. On one hand, the less viscous the material is, the better chance it has (1) to pass through a narrow bore of the applicator and into the channel and (2) to wet and fill the micro contours of the channels that it is filling. On the other, the more viscous the material is in the liquid state, (1) the less likely the material will run out of the vessel before it sets up and (2) the better it will suspend any filler or radio opaque substance that material may contain. The decision must be made on a case-by-case basis. A generally preferred place to start is with polymers that have molecular weights high enough to impart a viscosity of about 50,000 to 100,000 centipoise at 50° C. Filling very fine vessels using very fine cannula would suggest that a lower viscosity be used. Filling major bones such as a femur may well warrant the use of a much higher viscosity material.

The rate at which these polymers crystallize is extremely important to the practical application of the present invention. If the preplug crystallizes to quickly, it may even solidify in, say, the needle of the applicator. If it passes through he applicator it still may crystallize too fast in, say, the channel. A test of what is too rapid an onset of crystallization can be shown in this example: a channel such as the canaliculus of a dog is being occluded. A material that is being injected has a set time of 5 seconds. It takes 4 seconds for the polymeric material to flow through the needle stock. The first material to reach the canaliculus begins to harden after the first second. Additional material continues to be pumped into the canal at the same rate but now that the canaliculus is already partially blocked, the wall begins to extend beyond its normal dimension. A distended wall is a sign that the set time for this particular application is not long enough and that an adjustment in syntheses will be needed to provide material of longer set times.

If the set time is too long or if the melting point is too low, the material will never set up or will be washed away by the mechanical forces within the body or the universe before it has a chance to permanently occlude the channel in which it was placed. For an application such as occluding a canaliculus, an ideal crystallization set time is between one minute and ten minutes, preferably between two minutes and five minutes. By using such materials, the physician is given enough time to remove the device from a warming unit, insert the tip of the applicator into the punctum and inject the polymer composition into the canaliculus. The viscous nature will permit the polymer composition to remain in the liquid state where it was placed for five or ten minutes. Therefore, the polymer composition need not crystallize before then.

SPECIFIC CHARACTERISTICS AND FEATURES OF THE POLYMERS

Main chain crystalline polymers (MCCP's)

These materials have been studied for more than fifty years. Most of the better known commercial examples, such as polyethylene, are used below their crystalline melting point where they are tough and strong. Most successful commercial members have high first order transitions (usually within the range of 75° C. to 320° C.) in order to enjoy a broad use or service temperatures. Only those main chain crystalline polymers which have melting transitions between about 30° C. and about 50° C. can be considered for use in this application. Practically, the range is much narrower and is dictated by the normal body temperatures and the temperatures at which tissue injury occurs.

Specific examples of polymers falling in this narrowed melting transition range of about 34° C. to 45° C. are:

Poly-2,2,3,3,4,4-hexafluoro-(diamine)-pentamethylene adipate (34° C.)
Poly-tetramethylene succinate (34° C.)
Poly-N,N'diethyl-4,4'-methylenediphenylene sebacamide (34° C.)
Poly-trimethylene malonate (34° C.)
Poly-difluoro-methylene sulfide (35° C.)
Poly-N,N'-diisopropyl 2,2,3,3,4,4-hexafluoro-(diamine)-pentamethylene adipamide (35° C.)
Poly-oxacyclobutane (trimethylene oxide) (36° C.)
1,4-Poly-cis-2methyl-1,3-butadiene (36° C.)
Poly-4,methyl-(R+)-7, hydroxyenanthic acid (36° C.)
Poly-tetrahydrofuran (tetramethylene oxide) (37° C.)
Poly-trimethylene pimelate (37° C.)
Poly-tetramethylene azelaate (37° C.)
Poly-hexamethylenedithiotetramethylene disulfide (38° C.)
Poly-hexamethyleneoxymethylene oxide (38° C.)
Poly-trimethylene glutarate (39° C.)
Poly-tetramethylene disulfide (39° C.)
Poly-methyleneoxypentamethylene oxide (39° C.)
Poly-diethyl-dimethyl-(Si)-O-phenylene disiloxanylenedipropionamide (40° C.)
Poly-O-phenylene disiloxanylenedipropionamide (40° C.)
Poly-N,N'diethyl-4,4'-methyenediphenylene azelaamide (41° C.)
Poly-trimethylene suberate (41° C.)
Poly-cis-1,4-cyclohexylenedimethylene azelaate (41° C.)
Poly-pentamethylene azelaate (41° C.)
Poly-trans-1,4-cyclohexylenedimethylene Pimelate (42° C.)
Poly-tetrafluoro-ethylene oxide (42° C.)
Poly-isobutene (44° C.)
Poly-isotactic cis-1,3-pentadiene (44° C.)
Poly-pentamethylene disulfide (44° C.)
Poly-oxydiethylene sebacate (44° C.)
Poly-cyclopropylidenedimethylene oxide (45° C.)
Poly-ethylene p-(carboxyphenoxy)-caproate(45° C.)
Poly-N,N'-dibutyl-3,3'-dimethyl-(diamine)-4,4'-methyenediphenylene adipamide (45° C.)
Poly-N,N'-diisoamyl-3,3'-dimethyl-(diamine)-4,4'-methyenediphenylene adipamide (45° C.)
Poly-decamethylene disulfide (45° C.)
Poly-trimethylene adipate (45° C.)
Poly-2,2-dimethyl-(diol)-trimethylene adipate (45° C.)

Preferred main-chain crystallizable polymers include water-insoluble polyalkylene oxides, lower alkyl polyesters and polytetrahydrofuran.

Oligomeric MCCP's

The above are examples of homopolymers that have suitable first order transitions for the instant invention. Not mentioned are a myriad of copolymers that could be synthesized from various ratios of monomers that would exhibit first order transitions in this very temperature range. Of course, they too would be very applicable.

Smaller fragments of polymers known as oligomers can also be used in the present invention. For example short chain lengths of polymethylene, H—$(CH_2)_n$—H, exhibit melting transitions according to specific chain lengths.

When n=19 then Tm=32° C.–34° C.
n=20 then Tm=36° C.–38° C.
n=21 then Tm=40° C.–42° C.
n=22 then Tm=43° C.–45° C.
n=>$10^4$ then Tm=143° C.–145° C.

Hence, for many high molecular weight polymers whose melting point is above the desired and specified range, one need only produce the appropriate oligomer to obtain a transition of the correct temperature value.

Side-chain crystallizable polymers (SCCP's)

Side-chain crystallizable polymers, sometimes called "comb-like" polymers, are well-known and available commercially. These polymers are reviewed in *J. Polymer Sci.: Macromol. Rev.* 8:117–253 (1974), the disclosure of which is hereby incorporated by reference. In general, these polymers contain monomer units X of the formula:

wherein M is a backbone atom, S is a spacer unit and C is a crystallizable group. These polymers generally have a heat of fusion ($WH_f$) of at least about 10 Joules/g. The polymers can be copolymers and will contain 20 to 100 wt. % of the monomer units drawn above and are represented by "X". If the polymer contains less than 100% X, it will in addition contain monomer units which may be represented by "Y" or "Z", or both, wherein Y is any polar or nonpolar monomer or mixture of polar or nonpolar monomers capable of polymerizing with X and/or Z, and wherein Z is a polar monomer or mixture of polar monomers. These polar monomers—e.g., polyoxyalkylenes, acrylates including hydroxyethylacrylate, acrylamides and methacrylamides—will typically increase adhesion to most substrates. If the polar species "Z" is acrylic acid, it is preferred that it comprise about <10 wt. % of the polymer.

The backbone of the polymer (defined by "M") may be any organic structure (aliphatic or aromatic hydrocarbon, ester, ether, amide, etc.) or an inorganic structure (sulfide, phosphazine, silicone, etc.), and may include spacer linkages which can be any suitable organic or inorganic unit, for example ester, amide, hydrocarbon, phenyl, ether, or ionic salt (e.g., a carboxyl-alkyl ammonium or sulphonium or phosphonium ion pair or other known ionic salt pair).

The side-chain (defined by "S" and "C") may be aliphatic or aromatic or a combination of aliphatic and aromatic, but must be capable of entering into a crystalline state. Common examples are: linear aliphatic side-chains of at least 10 carbon atoms, e.g., $C_{14}$–$C_{22}$ acrylates or methacrylates, acrylamides or methacrylamides, vinyl ethers or esters, siloxanes or alpha olefins; fluorinated aliphatic side chains of at least 6 carbons; and p-alkyl styrene side chains wherein the alkyl is of 8 to 24 carbon atoms.

The length of the side-chain moiety is usually greater than 5 times the distance between side-chains in the case of acrylates, methacrylates, vinyl esters, acrylamides, methacrylamides, vinyl ethers and alpha olefins. In the extreme case of a fluoroacrylate alternate copolymer with butadiene, the side-chain can be as little as two times the length as the distance between the branches. In any case, the side-chain units should make up greater than 50% of the volume of the polymer, preferably greater than 65% of the volume.

Specific examples of side-chain crystallizable monomers are the acrylate, fluoroacrylate, methacrylate and vinyl ester polymers described in *J. Poly. Sci*, 10.3347 (1972); *J. Poly. Sci.* 10:1657 (1972); *J. Poly. Sci.* 9:3367 (1971); *J. Poly. Sci.* 9:3349 (1971); *J. Poly. Sci.* 9:1835 (1971); *J.A.C.S.* 76:6280 (1954); *J. Poly. Sci.* 7:3053 (1969); *Polymer J.* 17:991 (1985), corresponding acrylamides, substituted acrylamide and maleimide polymers (*J. Poly. Sci.: Poly. Physics Ed.* 11:2197 (1980); polyolefin polymers such as those described in *J. Poly. Sci.: Macromol. Rev.* 8:117–253 (1974) and *Macromolecules* 13:12 (1980), polyalkyl vinylethers, poly-alkylethylene oxides such as those described in *Macromolecules* 13:15 (1980), alkylphos phazene polymers, polyamino acids such as those described in *Poly. Sci. USSR* 21:241, *Macromolecules* 18:2141, polyisocyanates such as those described in *Macromolecules* 12:94 (1979), polyurethanes made by reacting amine- or alcohol-containing monomers with long-chain alkyl isocyanates, polyesters and polyethers, polysiloxanes and polysilanes such as those described in *Macromolecules* 19:611 (1986), and p-alkylstyrene polymers such as those described in *J.A.C.S.* 75:3326 (1953) and *J. Poly. Sci.* 60:19 (1962).

Of specific utility are polymers which are both relatively polar and capable of crystallization, but wherein the crystallizing portion is not affected by moisture. For example, incorporation of polyoxyethylene, polyoxypropylene, polyoxybutylene or copolyoxyalkylene units in the polymer will make the polymer more polar, improving adhesion to moist skin.

Hydrophilic monomers are beneficially added to the polymer if it is desired to increase the MVTR properties of the occluding material. Commonly used hydrophilic comonomers include acrylic acid, acrylamide, hydroxy alkyl (meth) acrylates such as hydroxy ethyl acrylate, hydroxy ethyl methacrylate and hydroxy butyl acrylate, alkoxy (meth) acrylates such as ethoxy ethyl acrylate, ethoxy ethoxy ethylacrylate, ethyltriglycol methacrylate, 3-methoxy butylacrylate and the like. A preferred class of high MVTR inducing monomers are derivatives of polyethylene glycol of with molecular weights ranging from 50 to 5,000. Commonly these units may be incorporated either into the backbone or as pendant groups.

Moisture vapor transmission rates and/or absorptive properties of the occluding material may be modified by the incorporation of soluble or insoluble hydrophilic materials, for example by addition of carboxymethyl cellulose, guar gum, carragenan, cellulose based or synthetic fibers and the like.

In a particularly preferred embodiment herein, in the above structure, —C is selected from the group consisting of —(CH$_2$)$_n$—CH$_3$ and —(CF$_2$)$_n$—CF$_2$H, where n is an integer in the range of 6 to 21 inclusive, —S— is selected from the group consisting of —O—, —CH$_2$—, —(CO)—, —O(CO)— and —NR— where R is hydrogen or lower alkyl (1°–16° C.), and —M— is —[(CH$_2$)$_m$—CH]— where m is 0 to 2.

Typical "Y" units include linear or branched alkyl or aryl acrylates or methacrylates, alpha olefins, linear or branched-.alkyl vinyl ether or vinyl esters, maleic esters or itaconic acid esters, acrylamides, styrenes or substituted styrenes, acrylic acid, methacrylic acid and hydrophilic monomers as detailed in WO84/0397, cited supra.

Some specific examples of side chain crystalline homopolymers which are suitable for inclusion in the present invention are:
Poly-dodecylvinyl ether (33° C.)
Poly-1,1-dihydroperfluoro-octyl-acrylate (35° C.)
Polycapryl-aldehyde (35° C.)
Poly-1-decene (40° C.)
Poly-trans-1,2-dichloro-dodecamethylene (40° C.),
Poly-vinyl palmitate (41° C.)
Poly-hexadecyl-acrylate (43° C.)
Poly-1-dodecene (45° C.)
Poly-N-hexadecyl-acrylamide (45° C.)

In addition to the above-described monomer units "M—S—C", monomer structures given by

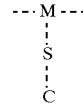

may in addition, or in the alternative, be present in the polymer as:

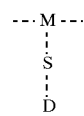

"D" is a hydrophilic polyether chain such as a polyoxyalkylene chain (e.g., polyoxyethylene) which, in contrast to "C", may or may not be crystallizable.

It is important in the case of polyolefins, which can exist in a plurality of tactic forms, that in order to effect the sharpness of transition between solid and liquid states the tacticity of the polymer must be carefully selected. The polymer can be present in a singular configuration, i.e., either atactic, syndiotactic or isotactic, but not in a mixture of tacticities unless their melting points opportunistically coincide. Having a mixture of various tacticpolymers with different melting points will broaden the transition and cause the resultant polymer to exhibit sluggish melting property changes over a narrow temperature range.

Random and block SCCP's

When two or more monomer units are used to synthesize the SCCP, it can be represented as:

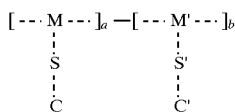

Here the two monomer units can be arranged randomly or in blocks. One or both of the units "a" and "b" may be crystalline.

Graft SCCP's

Still another way of utilizing or arranging these SCCP's is to graft them as hard blocks onto another backbone.
(—P—)

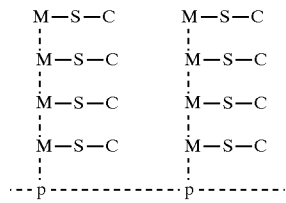

The backbone chain (—P—) can either be derived from an addition mechanism or from a condensation process. It could also be a side chain crystalline polymer but usually it will be a backbone without any ability to crystallize above room temperature. In that state it will be referred to as the "soft" block. In the present invention, we have used butyl acrylate as an example of the backbone chain. The grafted SCC blocks can be constructed of all the same monomer units or they could be random or block copolymers. In this present invention we have made examples in which the SCC block was either pure poly octadecyl ($C_{18}$) methacrylate or copolymers of octadecyl and docosyl ($C_{22}$) methacrylate. Furthermore, bimodal melting can be achieved by constructing grafts with some SCC moieties of pure octadecyl ester and with some SCC moieties of pure docosyl ester. The graft configuration of atoms offers a number of specific advantages which will be discussed below.

Control of first order transition temperature

Assuming that the graft consists of a SCCP block and a non crystalline backbone, the melting point will be determined entirely by the choice and ratio of monomers used to make up the hard block. Hence, sharp first order transitions can be achieved from about 34° C. when only octadecyl methacrylate derived blocks are used to about 45° C. when equal parts by weight of octadecyl and docosylmethacrylate are employed.

Control of recrystallization time

Most polymers that have melting points in the 30° C. to 50° C. temperature range will undergo crystallization within a few seconds after they have been lowered a few degrees below their normal melting temperature. By varying the ratio between soft non-crystalline backbone block and hard SCCP block, a kinetic lag can be built into the system. As an example, we are able to show that recrystallization times of 0–16 seconds @ 25° C. are exhibited when hard blocks of poly octadecylcohexyldecylacrylate are used and constitute 40 to 100% of the graft (Poly butyl acrylate is the soft block). When a hard block is changed from octadecyl acrylate to octadecyl methacrylate, the crystallization time of the block copolymer with 40% hard block lengthens to 73 seconds. It must be pointed out that all recrystallziation times were measures at 25° C. and that recrystallization time is shortened as the first order transition temperature is increased above the measuring temperature. When the concentration of hard block is further reduced to 30% and then to 20%, lag times of 97 and 154 seconds are achieved.

Experimental:

Melting temperatures were determined using Differential Scanning calorimetry (DSC) at a heating rate of 10° C./min.

Lag times or onset of crystallization are measured as follows: A sample of the material under test is melted and drawn down on a flat steel surface with a "blade" such that a uniformly thick film of 10µ is produced. The coated steel plate is then placed in an oven for 15 minutes and allowed to achieve a temperature of 60° C. The sample is removed and placed on a cooling plate that is maintained at 25° C. by means of thermostated, circulating water supply. A stop watch is begun immediately on contact. A small glass rod, 2 mm in diameter is dipped into the film and then pulled out. While the material is in the non-crystalline phase, small fine strings can be pulled from the film. As soon as the material experiences any significant amount of crystallization, it becomes impossible to pull anything from the surface. It is at this precise time when one observes the sharp transition from a flowable state to a non-flow one that the time is recorded.

EXAMPLES

The following examples are put forth so as to provide those of ordinary skill in the art with a complete disclosure and description of how to make and formulate polymers of the invention and are not intended to limit the scope of what the inventors regard as their invention. Efforts have been made to ensure accuracy with respect to numbers used (e.g., amounts, temperatures, molecular weights, etc.), but some experimental errors and deviation should be accounted for. Unless indicated otherwise, part are parts by weight, molecular weight is weight average molecular weight, temperature is in degrees centigrade and pressure is at or near atmospheric.

SPECIFIC EXAMPLES OF POLYMER FORMULATIONS

Example 1

Main chain crystalline polymer composites

A mixture of 93 parts of Poly-cis-isoprene (M.W. 800,000; Aldrich Chem Co.) and 7 parts of silver powder (Johnson Matthey) was made by adding the polymer and the filler to 100 parts of toluene, heating the suspension to about 75° C. and then stripping the solvent from the viscous mixture in a rotating evaporating unit under 21 mm Hg pressure. A constant temperature bath was used to keep the mixture above 70° C. When all the solvent was removed the temperature was lowered to 50° C. A glass rod was dipped into the viscous syrup. The temperature was allowed to cool slowly over the course of several hours. When the temperature cooled below 35° C., the rod was no longer able to be turned in relation to the mass of the polymer. The rod had become locked in place. The flask containing the composite and the rod was reheated to about 45° C. The rod could be easily extracted. The rod which now contained a thick coating of the composite was allowed to cool to room temperature. The coated rod was placed inside an anesthetized dogs mouth. The material proved to be radio-opaque and was clearly visible against other normal calcium based structures. This material is near the higher end of the spectrum of viscosities and rate of crystallization for such applications as a cast-in-place bone pin anchoring device. Lower molecular weight materials would flow easier and fill the surface interstices better and quicker.

Examples 2 to 6

The following materials were produced in a similar manner to those in example 1.

| Example # | Polymer (P) | Source | Filler (F) | Ratio F/P (Wt/Wt) | Melt Pt. |
|---|---|---|---|---|---|
| 2 | Poly-tetrahydrofuran | Polysciences | Fumed silica (.007µ) | 0.1 | 43° C. |
| 3 | Poly-tetrahydrofuran | Polysciences | none | n/a | 37° C. |
| 4 | Poly-trimethylene glutarate | Monomer Polymer & Dajac | none | n/a | 40° C. |
| 5 | Poly-trimethylene glutarate | Monomer Polymer & Dajac | Gold, powder, spherical, 1.5–3.0µ | 2.5 | 40° C. |
| 6 | Poly-trimethylene adapate | Monomer Polymer & Dajac | Silver powder | 1.5 | 45° C. |

These two polymers and three composites had viscosities which permitted them to be forced through a 16 gauge hypodermic needle when they were above the melting point. They all crystallized rapidly upon cooling to just below their melting point.

Examples 7 to 9

Use of an oligomeric fraction of Poly-methylene as a castable plug

A syringe fitted with a small blunted 24 gauge needle was filled with heneicosane, H—(CH$_2$)$_{21}$—H, after it was heated to 50° C. Viscosity=22 centipoise @ 3 RPM's and 50° C.; 21 centipoise @3 RPM's and 45° C. The air was removed by pointing the needle upward and pushing in the plunger until the hydrocarbon began to flow out of the tip. Immediately, the tip of the needle was inserted in the right punctum of the superior canaliculus of a beagle dog, tranquilized with a solution of acepromazine, and about 10 mg of the oligomer was introduced. The material instantly set up into a solid mass beneath the thin semi-transparent tissue surrounding the punctum. The experiment was repeated only this time the heneicosane contained three times its weight of Gold, (powder, spherical, 1.5–3.0µ). Some difficulty was experienced because the gold would tend to settle out while the olefin was in the liquid state. Nevertheless, some of the suspension was introduced into the left punctum of the superior canaliculus of the same beagle dog and was corroborated by X-ray radiography. The settling of this type of suspension was reduced significantly when fumed silica was added to the mixture. Unfortunately, the more silica that was added the more difficult it became to force the mixture through the very fine needle. This oligomeric material represents the lower end of the spectrum of viscosities for such applications as a cast-in-place device.

| Example # | Polymer (P) | Source | Filler (F) | Ratio F/P (Wt/Wt) | Melt Pt. |
|---|---|---|---|---|---|
| 7 | heniecosane | Aldrich Chem Co. | none | n/a | 43° C. |
| 8 | heniecosane | Aldrich Chem Co. | Gold, powder, spherical, 1.5–3.0µ | 3.0 | 37° C. |
| 9 | heniecosane | Aldrich Chem Co. | Gold + Fumed silica (.007µ) | 3.1 | 40° C. |

Example 10

Preparation of side chain crystalline polymer

A mixture was prepared from 84 parts octadecyl acrylate containing at least 90% octadecyl chains (with all the remaining chains greater than 14 carbon atoms in length), 16 parts butyl acrylate and 1.86 parts dodecyl mercaptan. To a reactor maintained at 100° C. was added this mixture at a rate of 14.5 ml/min simultaneously with t-butyl peroctoate that was added at a rate of 0.15 ml/min. The reaction mixture was allowed to react for an additional 2 hours after the addition was complete. The product was removed from the reactor and underwent multiple (2x) reprecipitations from a solvent/nonsolvent mixture (toluene/ethanol). The final purified product was dried under reduced pressure yielding 80 parts of sample 10. GPC analysis against polystyrene standards yields an Mw=18,900, Mn=11,800 and Mw/Mn=1.6. Extraction analysis yielded the following residuals: 374 ppm of octadecyl acrylate and <130 ppm of butyl acrylate. DSC analysis shows a first heat endothermic peak at 40.5° C. and second heat endothermic peak at 38.6° C. Viscosity analysis on a Brookfield LVT viscometer using spindle 18/13R yielded the following viscosities: 1530 centipoise @ 0.3 RPM's and 50° C.; 2300 centipoise @ 0.3 RPM's and 45° C.

Examples 11 to 17

The following materials were produced in a similar manner to that in example 10. The appropriate choice of reactant ratios and different side chain lengths allows variation of the SCC polymer melt temperature throughout the bioeffective range of about 30°–50° C.

| Sample # | Formulation (parts by wt.) C18A/C4A/C12SH | Mw (Daltons) | Second Heat Tm (°C.) |
|---|---|---|---|
| 11 | 96/4/1.86 | 16,800 | 44.5 |
| 12 | 92/8/1.86 | 19,600 | 44.5 |
| 13 | 89/11/1.86 | 20,500 | 40.2 |
| 14 | 88/12/1.86 | 21,800 | 40.6 |
| 15 | 86/14/1.86 | 31,300 | 38.4 |
| 16 | 80/20/1.86 | 17,900 | 36.3 |
| 17 | 76/24/1.86 | 17,900 | 35.0 |

Example 18

Preparation of the polyoctadecyl-cohexadecyl acrylate hard block. (macromer) A solution was prepared from 92 g octadecyl acrylate (minimum 95% octadecyl chains), 8 g of hexadecyl acrylate (minimum 95% hexadecyl chains) 3.8 g mercaptoethanol, 200 ml toluene and 1.0 g azobisisobutyronitrile (AIBN). The stirred solution was heated to 60° C. under a nitrogen blanket for 14 hours. The solution was then heated to destroy residual AIBN followed by addition of 8.5 g isocyanatoethylmethacrylate. One drop of dibutyl tin dilaurate was added. Stirring at room temperature was continued for 16 hours. The polyoctadecyl methacrylate macromer was precipitated from the solution with ethanol.

It was filtered and dried under reduced pressure. GPC analysis indicated the following: Mw=3888, Mn=2936 and Mw/Mn=1.32. DSC analysis shows a second heat endothermic peak at 41.6° C.

Examples 19 to 25
Preparation of other hard block macromers

They have been prepared to vary the Tm within the bioeffective range. Tm variation within the bioeffective range is readily accomplished through appropriate choice of polymer side chain length. The following materials were produced in a similar manner to that in example 18.

| Sample # | Formulation (% by wt) | | | | Mw | 2nd Heat Tm(°C.) |
|---|---|---|---|---|---|---|
| | C16A | C18A | C18M | C22M | | |
| 19 | | 100 | | | 3900 | 44.8 |
| 20 | | 0 | 100 | | 3900 | 35.6 |
| 21 | | | 15 | 85 | 3600 | 35.7 |
| 22 | | | 25 | 75 | 3900 | 36.8 |
| 23 | | | 66 | 34 | 4300 | 41.8 |
| 24 | | | 60 | 40 | 3400 | 37.43 |
| 25 | 8 | 92 | 55 | 45 | 3900 | 41.62 |

Example 26
Preparation of SCC polymer Thermoplastic Elastomer (TPE)

A graft copolymer (polybutyl acrylate-g-polyoctadecyl acrylate) was prepared using the polyoctadecyl acrylate macromer of example 18. A solution was prepared from 20 g of the above macromer, 30 g of butyl acrylate, 100 ml of toluene, 0.2 g of dodecyl mercaptan and 0.5 g of AIBN. The solution was heated to 60° C. under nitrogen blanket for 14 hours. The TPE graft copolymer was precipitated from solution with cold ethanol, filtered and dried under reduced pressure to yield 40 g of the product sample. GPC analysis indicates the following: Mw=40,400 Mn=18,000 and Mw/Mn=2.24. Residue analysis indicates; butyl acrylate 624 ppm; octadecyl methacrylate 562 ppm. DSC analysis shows a second heat endothermic peak at 41.3° C. Time @ 25° C. to onset of crystallization=16 seconds. Viscosity (LVT w/spindle #4)=7200 centipoise @ 3 RPM's and 50° C.; 16000 centipoise @ 3 RPM's and 46° C.

Examples 27 to 40
Preparation of other Graft SCC polymers (Thermoplastic Elastomers)

These polymers have been prepared to vary the Tm within the bioeffective range as well as the onset of crystallization time. Tm variation within the bioeffective range is readily accomplished through appropriate choice of polymer side chain length and the relative ratio between the hard and soft block. The following materials were produced in a similar manner to that in example 26.

| Sample # | Macromer | Macromer to C4A ratio | Mw | Second Heat Tm(°C.) | Time @ 25° C. to onset of crystallization |
|---|---|---|---|---|---|
| 27 | 19 | 40/60 | 184,000 | 43.0 | >15 |
| 28 | 19 | 40/60 | 48,000 | 41.7 | >15 |
| 29 | 19 | 40/60 | 103,00 | 42.7 | >15 |
| 30 | 20 | 40/60 | 40,000 | 41.3 | 16 |
| 31 | 20 | 40/60 | 80,000 | 41.3 | 24 |
| 32 | 21 | 40/60 | 48,000 | 32.8 | 54 |
| 33 | 22 | 40/60 | 52,000 | 32.8 | 29 |
| 34 | 22 | 30/70 | 56,000 | 31.7 | 51 |
| 35 | 18 | 30/70 | 55,000 | 28.9 | 97 |
| 36 | 22 | 20/80 | 57,000 | 31.4 | 135 |
| 37 | 18 | 20/80 | 53,000 | 28.8 | 154 |
| 38 | 23 | 40/60 | 54,900 | 42.8 | 25 |
| 39 | 23 | 30/70 | 63,800 | 41.9 | 25 |
| 40 | 23 | 20/80 | 63,100 | 40.3 | 17 |
| 41 | 23 | 30/70 | 95,500 | 43.0 | 20 |

Example 42

Material made in example 41 was blended with gold (powder, spherical, 1.5–3.0μ) power as described in example 5. The composite was heated to 50° C. and loaded into a small hydraulic applicator with an exit port consisting of a drilled hole using a number 80 drill. The applicator and its charge were allowed to cool. At room temperature no material could be released from the applicator even when high pressure was exerted. The applicator and its charge was then heated in a cup of warm water (~50° C.). The tip of the applicator was inserted in the left punctum of the superior canaliculus of a beagle dog that had been tranquilized with a solution of acepromazine and about 10 mg of the composite was introduced through the narrow portal. The material flowed into the canaliculus beneath the thin semi-transparent tissue surrounding the punctum. Within a few minutes the dog was x-rayed and the plug was clearly seen. After 60 day, the plug remained in exactly the same position. At this time 10 cc of warm (46° C.) isotonic sterile saline solution was used to flush out the cast-in-place-plug.

Example 43

Experiment 42 was repeated only using the polymeric material produced in example 33. When an x-ray was taken after 3 hours, a plug was clearly visible. When an x-ray was taken after 48 hours, there was no evidence of any plug remaining. It can be deduced that, for this area of the mammalian body, the particular sample possessed a melting point that was below the normal tissue temperature. Therefore, it never resolidified and was unstable. On the other hand, the experiment described in example 42 demonstrates that stabilization of the position within the canaliculus by recrystallization of sample 41 did occur.

The instant invention is shown and described herein in what is considered to be the most practical, and preferred embodiments. It is recognized, however, that departures may be made therefrom which are within the scope of the invention and that obvious modifications will occur to one skilled in the art upon reading this disclosure.

I claim:

1. A channel occluding unit for occluding a channel having a maximum temperature $T_L$ in a living mammal, the unit comprising an injecting device; and a thermoplastic, biocompatible, non-immunogenic occluding composition in the injecting device, the composition,
  (a) having a melting point which is
    (i) below 50° C. and
    (ii) such that the composition is flowable at a temperature which does not damage the channel,
  (b) having a freezing point which is (i) above 30° C. and
(ii) such that the composition is non flowable at $T_L$,
(c) comprising a thermoplastic polymer, and
(d) being injectable, while it is flowable, from the device into the channel, to form a plug which occludes the channel and which can be removed from the channel by heating to a temperature at which the composition is flowable.

2. A channel occluding unit of claim 1 wherein the polymer is a polymer which, when cooled from above the melting point to below the freezing point, becomes a crystalline solid.

3. The channel occluding unit of claim 1, further comprising:
a means for heating the occluding composition within the injecting device to a temperature such that the occluding composition becomes flowable.

4. The channel occluding unit of claim 1, wherein the occluding composition is a non-flowable solid at a temperature of about 45° C. or less and is flowable at a temperature of about 46° C. or more.

5. The channel occluding unit of claim 1, wherein the occluding composition is flowable at a temperature of 10° C. or less above the body temperature of the mammal and is non-flowable at the body temperature of the mammal.

6. The channel occluding unit of claim 1, wherein the polymer is selected from the group consisting of a mainchain crystalline polymer; and a graft copolymer.

7. The channel occluding unit of claim 1, wherein the polymer is a sidechain crystalline polymer having a melting point between 34° and 45° C.

8. The channel occluding unit of claim 1 wherein the polymer is a thermoplastic elastomer comprising
(i) a backbone which does not crystallize above room temperature, and
(ii) sidechain crystalline polymeric blocks which extend from the backbone.

9. A device for occluding a channel in a human being, the channel having a maximum temperature $T_L$, the device comprising
a chamber having at least one orifice therein;
a thermoplastic, biocompatible, non-immunogenic occluding composition in the chamber, the occluding composition having a melting point which is
(i) sufficiently high that the occluding composition is non-flowable at temperatures experienced by human beings, and
(ii) sufficiently low that it can be melted and brought into contact with the cells of a human being without damaging the cells,
the occluding composition being (a) non-flowable at $T_L$, and (b) flowable when heated to a temperature which does not damage the channel, and the occluding composition comprising a thermoplastic polymer; and
a means for propelling the occluding composition out of the chamber, through the orifice, and into the channel, to form a plug which occludes the channel and which can be removed from the channel by heating to a temperature at which the composition is flowable.

10. The device of claim 9, further comprising:
a means for raising the temperature of the occluding composition to a temperature where the occluding composition becomes flowable.

11. The device of claim 9 wherein the polymer is a sidechain crystalline polymer having a melting point between 34° and 45° C.

12. The device of claim 9 wherein the polymer is a thermoplastic elastomer comprising
(i) a backbone which does not crystallize above room temperature, and
(ii) sidechain crystalline polymeric blocks which extend from the backbone.

13. A device for occluding a channel in a living mammal, the channel having a maximum temperature $T_L$, the device comprising:
(a) an injector comprising a chamber;
(b) a thermoplastic, biocompatible, non-immunogenic occluding composition within the chamber, the occluding composition having a melting point which is
(i) sufficiently high that the occluding composition is non-flowable at $T_L$, and
(ii) sufficiently low that melted occluding composition can be injected into the channel without damaging the mammal; and
(c) means for removing melted occluding composition from the chamber and injecting it into the channel in a sufficient quantity to form a plug which at least partially occludes the channel and which can be removed from the channel by heating to a temperature at which the composition is flowable.

14. The device of claim 13 including means for heating the occluding composition in the chamber to a temperature higher than the melting point of the occluding composition.

15. The device of claim 13 wherein the polymer is a sidechain crystalline polymer having a melting point between 34° and 45° C.

16. The device of claim 13 wherein the polymer is a thermoplastic elastomer comprising
(i) a backbone which does not crystallize above room temperature, and
(ii) sidechain crystalline polymeric blocks which extend from the backbone.

17. A device for occluding a *canaliculus lacrimalis* in a human being, the device comprising
(a) a chamber,
(b) within the chamber, a thermoplastic, biocompatible, non-immunogenic occluding composition comprising a sidechain crystalline polymer having a melting point between 38° and 43° C.;
(c) a heater for melting the occluding composition within the chamber; and
(d) means for removing melted occluding composition from the chamber and injecting it into the *canaliculus lacrimalis*.

18. A device according to claim 17 wherein the polymer is a thermoplastic elastomer comprising
(i) a backbone which does not crystallize above room temperature, and
(ii) sidechain crystalline polymeric blocks which extend from the backbone.

19. A device according to claim 18 wherein the occluding composition contains particles of gold as a filler.

* * * * *